(12) United States Patent
Kakitani

(10) Patent No.: US 9,289,393 B2
(45) Date of Patent: Mar. 22, 2016

(54) SINGLE STROKE COMPRESSION MOLDING MACHINE AND METHOD OF PRODUCING COMPRESSION MOLDED PRODUCT

(71) Applicant: Kikusui Seisakusho, Ltd., Kyoto-shi (JP)

(72) Inventor: Tomohiro Kakitani, Kyoto (JP)

(73) Assignee: KIKUSUI SEISAKUSHO, LTD., Kyoto-Shi, Kyoto (JP)

( * ) Notice: Subject to any disclaimer, the term of this patent is extended or adjusted under 35 U.S.C. 154(b) by 0 days.

(21) Appl. No.: 14/598,960

(22) Filed: Jan. 16, 2015

(65) Prior Publication Data
US 2015/0216805 A1     Aug. 6, 2015

(30) Foreign Application Priority Data

Feb. 4, 2014   (JP) ................................. 2014-019812

(51) Int. Cl.
| | | |
|---|---|---|
| *B30B 11/08* | (2006.01) | |
| *B30B 15/00* | (2006.01) | |
| *A61K 9/20* | (2006.01) | |
| *B30B 11/34* | (2006.01) | |
| *B30B 15/30* | (2006.01) | |

(52) U.S. Cl.
CPC .............. *A61K 9/2095* (2013.01); *A61K 9/2086* (2013.01); *B30B 11/08* (2013.01); *B30B 11/085* (2013.01); *B30B 11/34* (2013.01); *B30B 15/0082* (2013.01); *B30B 15/304* (2013.01)

(58) Field of Classification Search
None
See application file for complete search history.

(56) References Cited

U.S. PATENT DOCUMENTS

| | | | | | |
|---|---|---|---|---|---|
| 3,999,922 | A | * | 12/1976 | Shimada | ........................ 425/210 |
| 4,259,049 | A | * | 3/1981 | Willich | ........................... 425/73 |
| 4,793,791 | A | * | 12/1988 | Kokuryo | ........................ 425/345 |

FOREIGN PATENT DOCUMENTS

| | | |
|---|---|---|
| DE | 24 35 777 A1 | 2/1976 |
| JP | 2009-95855 A | 5/2009 |
| JP | 2009-095855 A | 5/2009 |
| JP | 2011-218432 A | 11/2011 |
| JP | 2011-236447 A | 11/2011 |
| JP | 2011-255397 A | 12/2011 |
| JP | 2013-043212 A | 3/2013 |

\* cited by examiner

*Primary Examiner* — Mary F Theisen
(74) *Attorney, Agent, or Firm* — McGinn IP Law Group, PLLC

(57) ABSTRACT

The invention provides a single stroke compression molding machine including: a die table having a die bore penetrating vertically; a slidable lower punch located below the die bore and having an upper end to be inserted to the die bore; a slidable upper punch located above the die bore to face the lower punch and having a lower end to be inserted to the die bore; and a dust collector configured to collect dust on an upper surface of the die table in a state where the lower end of the upper punch is located in the die bore.

16 Claims, 8 Drawing Sheets

SINGLE STROKE COMPRESSION MOLDING MACHINE AND METHOD OF PRODUCING COMPRESSION MOLDED PRODUCT

BACKGROUND

A rotary compression molding machine that can mass-produce tablets has been typically used in the pharmaceutical field in recent years. The rotary compression molding machine includes a rotary die table having die bores, and upper punches and lower punches that are retained respectively above and below the die bores so as to be slidable upward and downward. The rotary compression molding machine causes the die table and the punches to horizontally rotate together and compression molds a powdery material filled in the die bores when the upper punches and the lower punches pass between upper and lower rolls (see Japanese Unexamined Patent Publications JP 2009-095855 A, JP 2011-218432 A, and JP 2011-255397 A, for example).

A small rotary compression molding machine is often used at a research and development stage. Such a compression molding machine is not required to have very high production performance at the research and development stage. The compression molding machine is required instead to have versatility and multifunctionality so as to produce various types of tablets such as double layer tablets, triple layer tablets, and dry-coated tablets.

Providing multifunctionality even to a small rotary compression molding machine causes a heavy burden in terms of cost.

Considered accordingly was a configuration of a single stroke compression molding machine satisfying the above requirements.

Japanese Unexamined Patent Publication JP 2013-043212 A discloses a configuration for production of a double layer molded product, in which a first powder supplier moves to a position above a die, supplies the die with a powder for a first layer, and moves from the position above the die. A second powder supplier subsequently moves to the position above the die, supplies the die with a powder for a second layer, and moves from the position above the die. An upper punch and a lower punch then compression mold the powders in the die.

In the configuration disclosed in JP 2013-043212 A, the powder left on a die table by the first powder supplier and the powder left on the die table by the second powder supplier are mixed together to cause contamination by these powders.

JP 2009-095855 A discloses a rotary compression molding machine configured to produce a triple layer tablet supplies a die bore with powders for second and third layers and sucks to remove the powders out of the die bore using a dust collector before the powders are compression molded, in order to eject only a compression molded first layer portion or the like at an ordinary molded product ejecting position as a sample.

The technique disclosed in JP 2009-095855 A is sucking to remove the powders once fed into the die bore out of the die bore before the powders are compression molded. This technique fails to remove an unnecessary powder remaining on a rotating die table so as to prevent contamination by the powders.

JP 2011-218432 A discloses a method of removing an unnecessary powdery material remaining on a rotating die table of a rotary compression molding machine. Specifically, a cleaning powdery material is supplied on the die table and is agitated by an agitating blade of a cleaning device to clean the rotating die table, and an unnecessary powdery material as well as the cleaning powdery material are removed by a dust collecting mechanism.

The cleaning device described in JP 2011-218432 A cleans the rotating die table after a completed molded product is ejected from a die bore. The cleaning device does not clean the rotating die table during production of the molded product, particularly, after a first feeder fills a powdery material for a first layer and before a second feeder fills a powdery material for a second layer. The cleaning device thus fails to prevent contamination by these powdery materials.

JP 2011-255397 A discloses a rotary compression molding apparatus configured to produce a dry-coated tablet as a molded product having a core (an internal core or a core tablet) buried therein. Specifically, a transfer disc of a core supplier is rotated in synchronization with rotation of a rotating die table by a servo motor, and the core tablet is supplied from the transfer disc into a die bore in the rotating die table.

However, a single stroke compression molding machine does not include any rotating die table, and does not need to rotate a rotating die table having die bores in synchronization with a transfer disc configured to supply each of the die bores with a core. The mechanism disclosed in JP 2011-255397 A is not applicable to the single stroke compression molding machine.

SUMMARY OF THE INVENTION

An object of the invention is to suitably prevent contamination by a powdery material remaining on a die table in a single stroke compression molding machine configured to produce a molded product such as a double layer tablet, a triple layer tablet, or a dry-coated tablet, and approximate to a compression molding condition for a rotary compression molding machine.

According to the invention, a single stroke compression molding machine includes: a die table having a die bore penetrating vertically; a slidable lower punch located below the die bore and having an upper end to be inserted to the die bore; a slidable upper punch located above the die bore to face the lower punch and having a lower end to be inserted to the die bore; a feeder configured to fill the die bore with a powdery material to be compression molded by the lower and upper punches; and a dust collector configured to collect dust on an upper surface of the die table in a state where the lower end of the upper punch is located in the die bore. The powdery material in the invention refers to an aggregate of minute solids and includes an aggregate of particles such as what they call granules and an aggregate of powder smaller than the particles.

The lower and upper punches are preferred to be applicable to a rotary compression molding machine (particularly conform to the TSM Standards or the EU Standards). This configuration achieves approximation to a compression molding condition for a rotary compression molding machine.

Optionally, a single stroke compression molding machine including: a die table having a die bore penetrating vertically; a slidable lower punch located below the die bore and having an upper end to be inserted to the die bore; a slidable upper punch located above the die bore to face the lower punch and having a lower end to be inserted to the die bore; a feeder configured to fill the die bore with a powdery material to be compression molded by the lower and upper punches; and a dust collector configured to collect dust on an upper surface of the die table; wherein the dust collector includes a driver configured to move upward or downward along with the upper punch, a dust collecting case engaged with the driver and configured to move upward or downward, in accordance with upward or downward movement of the driver, between a dust collecting position where the dust collecting case covers a region around the die bore on the upper surface of the die table and a retreating position where the dust collecting case is distant above from the upper surface of the die table, and a suction duct connected to the dust collecting case and configured to decompress an internal space of the dust collecting case.

In order for production of a molded product such as a double layer tablet, a triple layer tablet, or a dry-coated tablet, the feeder preferably includes at least two feeders.

In order to produce a molded product such as a dry-coated tablet having a core inside the powdery material, the single stroke compression molding machine preferably includes a supplier configured to supply the die bore with the core.

A method of producing a compression molded product according to the invention relates to a method of producing a molded product in a single stroke compression molding machine by compression molding a powdery material filled in a die bore provided in a die table with a lower punch having an upper end inserted to the die bore and an upper punch having a lower end inserted to the die bore, and the method includes collecting dust on an upper surface of the die table in a state where the lower end of the upper punch is located in the die bore.

A method of producing a compression molded product such as a double layer tablet according to the invention relates to a method of producing a molded product in a single stroke compression molding machine by compression molding a powdery material filled in a die bore provided in a die table with a lower punch having an upper end inserted to the die bore and an upper punch having a lower end inserted to the die bore, and the method includes: firstly filling a powdery material into the die bore; firstly compressing the powdery material with the lower end of the upper punch inserted to the die bore after the first filling; collecting dust on an upper surface of the die table in a state where the lower end of the upper punch is located in the die bore; secondly filling a powdery material into the die bore after the dust collection; and secondly compressing the powdery material with the lower end of the upper punch inserted to the die bore after the second filling.

A method of producing a compression molded product such as a dry-coated tablet according to the invention relates to a method of producing a molded product having a core inside a powdery material in a single stroke compression molding machine by compression molding a powdery material filled in a die bore provided in a die table with a lower punch having an upper end inserted to the die bore and an upper punch having a lower end inserted to the die bore, and the method includes: firstly filling a powdery material into the die bore; collecting dust on an upper surface of the die table in a state where the lower end of the upper punch is located in the die bore after the first filling; supplying a core into the die bore after the dust collection; secondly filling a powdery material into the die bore after the supply; and secondly compressing the powdery materials with the lower end of the upper punch inserted to the die bore after the supply and the second filling.

The method of producing the molded product in the single stroke compression molding machine by compression molding the powdery material filled in the die bore provided in the die table with the lower punch having the upper end inserted to the die bore and the upper punch having the lower end inserted to the die bore preferably includes compression molding the powdery material filled in the die bore with lower and upper punches that are applicable to a rotary compression molding machine.

DESCRIPTION OF THE PREFERRED EMBODIMENTS

Figure 1:
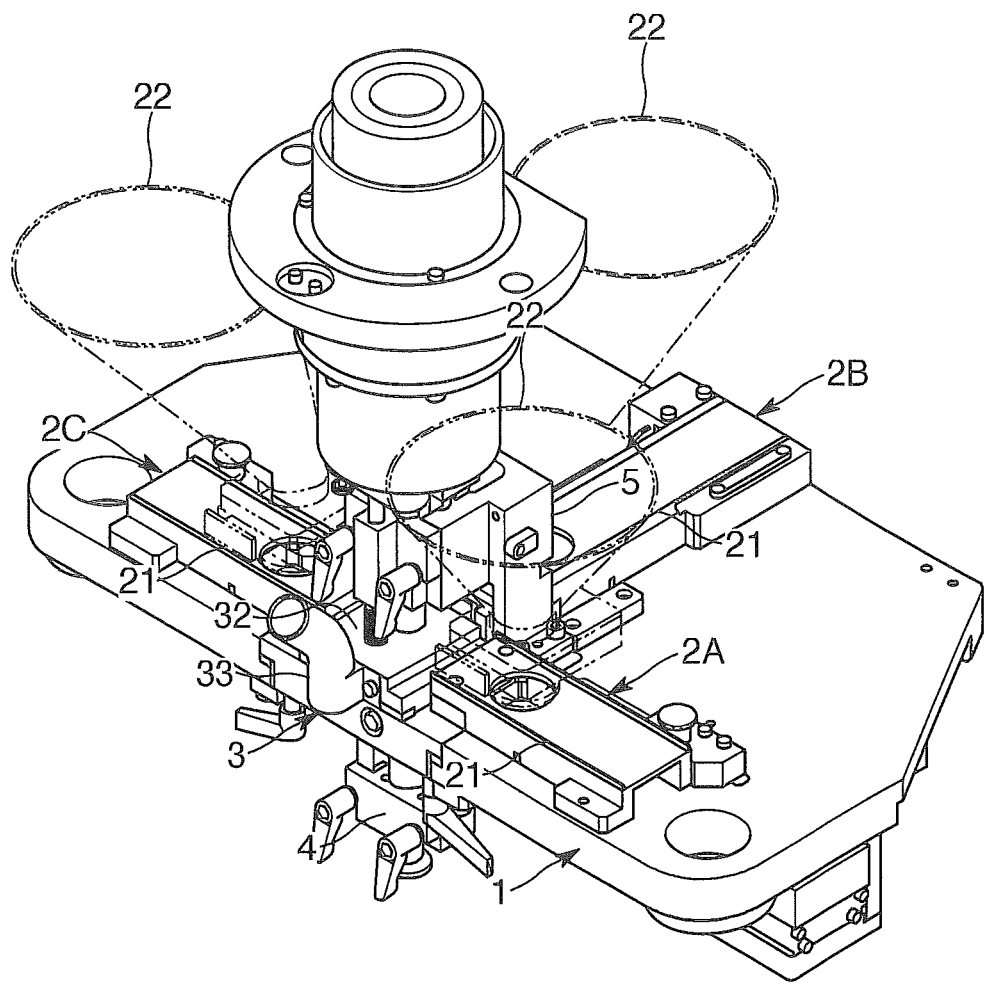
FIG. 1 is a perspective view of a single stroke compression molding machine according to an embodiment of the invention.

Embodiments of the invention will now be described with reference to the drawings. A compression molding machine according to the embodiment relates to a single stroke compression molding machine configured to produce a compression molded product such as a double layer tablet, a triple layer tablet, or a dry-coated tablet. The compression molding machine is provided mainly to a research and development site.

As shown in FIGS. 1 to 5, the compression molding machine according to the embodiment principally includes a die table 1 having a die bore 12 to be filled with a powdery material, a lower punch 6 located below the die bore 12 and configured to compress the powdery material filled in the die bore 12, an upper punch 7 located above the die bore 12 so as to face the lower punch 6 and configured to compress the powdery material filled in the die bore 12 along with the lower punch 6, feeders (feed shoe) 2A, 2B, and 2C each configured to fill the die bore 12 with a powdery material, and a dust collector 3 configured to collect dust on the upper surface of the die table 1.

The die table 1 is provided with a die installation portion 13 into which a die 11 is mounted. The die 11 has the die bore 12 penetrating vertically, and conforms to the TSM Standards or the EU Standards. The die 11 is also applicable to a rotary compression molding machine that has been developed from the compression molding machine according to the embodiment and is configured for mass production of compression molded products. The die table 1 can be directly provided with the die bore 12 penetrating vertically, instead of having the die 11.

The lower punch 6 is retained at a lower punch retaining portion 4 such that the upper end (punch tip) thereof is inserted to the die bore 12 and is slidable relatively to the die bore 12. The upper end of the lower punch 6 is constantly inserted to the die bore 12. The lower punch 6 is reciprocated upward and downward by a drive source such as a servo motor (not shown).

The upper punch 7 is retained at an upper punch retaining portion 5 such that the lower end (punch tip) thereof is inserted to the die bore 12 and is slidable relatively to the die bore 12. The lower end of the upper punch 7 enters and exits the die bore 12. The upper punch 7 is also reciprocated upward and downward by a drive source such as a servo motor (not shown).

Like the die 11, the lower punch 6 and the upper punch 7 each conform to the TSM Standards or the EU Standards. The lower punch 6 and the upper punch 7 are also applicable to a rotary compression molding machine.

A hopper 22 has the upper portion expanding upward like a funnel. When the hopper is fed with a powdery material to be compression molded by the lower punch 6 and the upper punch 7, the powdery material is supplied to each of the feeders 2A, 2B, and 2C.

The feeders 2A, 2B, and 2C slide relatively to the upper surface of the die table 1 and fill the die bore 12 with the powdery material. Each of the feeders 2A, 2B, and 2C has a plate shape and includes a filling portion 211 having an inner diameter sufficiently larger than that of the die bore 12 and penetrating vertically, and a leveling plate 212.

Each of the feeders 2A, 2B, and 2C is reciprocated by a drive source such as a servomotor (not shown) between a filling position (the position indicated in FIG. 4) where the die bore 12 is filled with a powdery material and a supplying position (the position indicated in FIGS. 2, 3, and 5) where the hopper 22 supplies the filling portion 211 with a powdery material. Each of the feeders 2A, 2B, and 2C located at the filling position covers a region around the die bore 12 on the upper surface of the die table 1. At the same time, the filling portion 211 is positioned vertically above the die bore 12 and the powdery material in the filling portion 211 is filled into the die bore 12.

In contrast, each of the feeders 2A, 2B, and 2C located at the supplying position moves from the region around the die bore 12 on the upper surface of the die table 1. At the same time, the filling portion 211 is positioned vertically below the hopper 22 and receives the powdery material stored in the hopper 22.

After the filling portion 211 fills the powdery material into the die bore 12, the leveling plate 212 levels the powdery material overflown from the die bore 12 due to upward movement of the lower punch 6 and removes the excessive powdery material on the die bore 12.

As shown in FIG. 1, the single stroke compression molding machine according to the embodiment includes the feeders 2A, 2B, and 2C that reciprocate relatively to the die bore 12 in three different directions when viewed from the die bore 12 and fill the die bore 12 with powdery materials. The feeders 2A, 2B, and 2C are in common in terms of the structure and the mechanism as described above. The hoppers 22 in the feeders 2A, 2B, and 2C can be fed with different types of powdery materials or a same powdery material.

The dust collector 3 includes a driver 31 configured to move upward and downward along with the upper punch 7, a dust collecting case 32 configured to move upward and downward along with the upper punch 7 by means of the driver 31 to cover the region around the die bore 12 on the upper surface of the die table 1, and a suction duct 33 connected to the dust collecting case 32 and configured to decompress the dust collecting case 32.

The driver 31 according to the embodiment has a vertically extending shaft shape in parallel with the upper punch 7, and is retained at the retaining portion 5 that also retains the upper punch 7. The upper end of the driver 31 is coupled to the drive source such as a servo motor as the upper end of the upper punch 7 is, and reciprocates upward and downward along with the upper punch 7. Unlike the upper punch 7, the driver 31 can be displaced within a certain range in the vertical direction relatively to the drive source.

The dust collecting case 32 has an upper wall 321 and side walls 322 extending downward from the peripheral edges of the upper wall 321 so as to surround an internal space 323. The dust collecting case 32 has a thin box shape with an open bottom face. The upper wall 321 has a portion located vertically above the die bore 12 and having a punch insertion bore 324 that penetrates vertically and allows the upper punch 7 to be inserted therethrough. The upper wall 321 also has a portion located vertically below the driver 31 and having an engagement bore 325 that is engaged with the lower end of the driver 31.

The upper surface of the upper wall 321 of the dust collecting case 32 vertically faces the lower surface of the upper punch retaining portion 5. A biasing member 34 exerting elastic bias force is provided between the dust collecting case 32 and the upper punch retaining portion 5. The biasing member 34 is provided to press the dust collecting case 32 so as to come into close contact with the upper surface of the die table 1 during dust collection. The biasing member according to the embodiment is a compression coil spring 34 that is elastically deformable and is wound around the driver 31.

Figure 2:
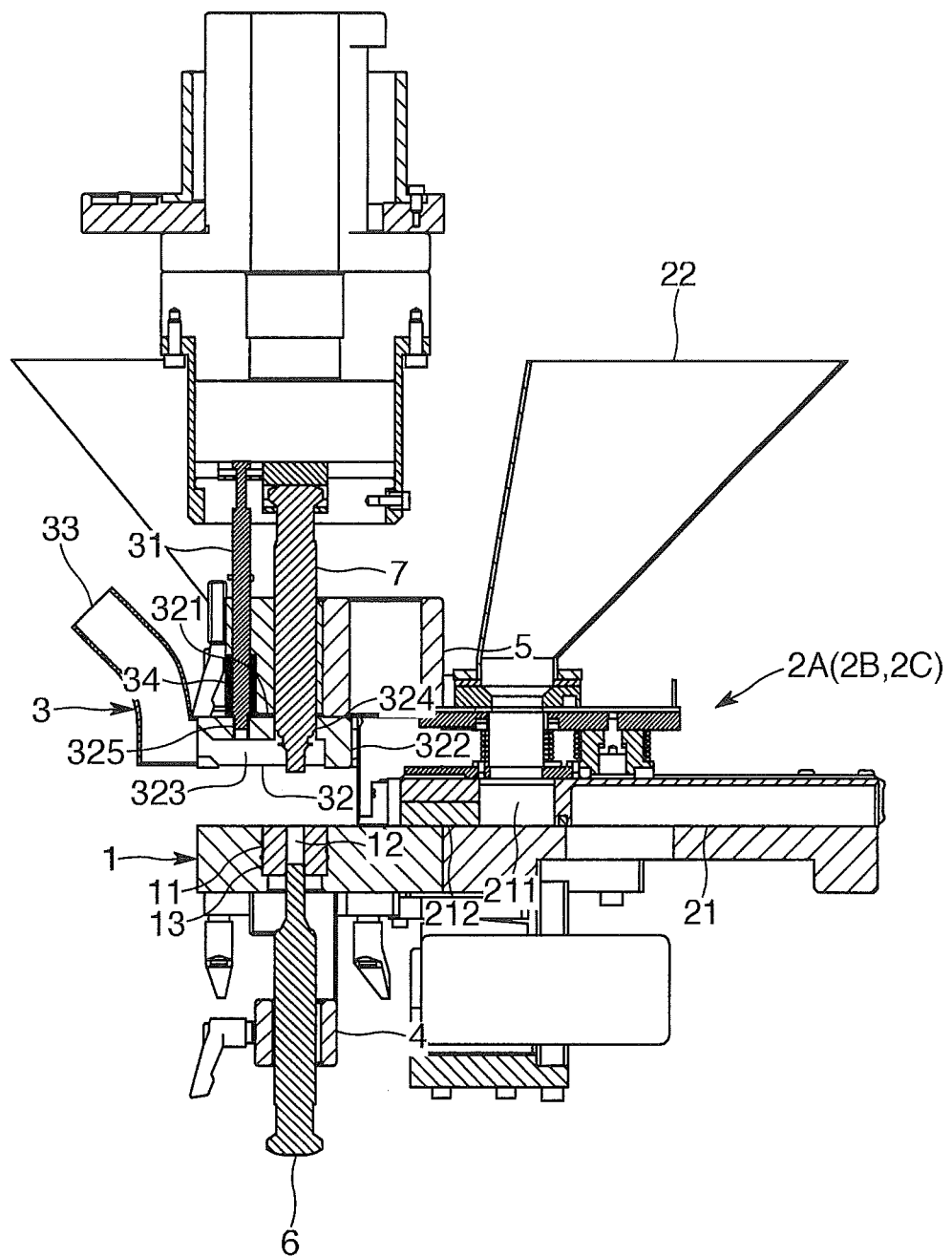
FIG. 2 is a side sectional view of a principal part in the compression molding machine.
Figure 3:
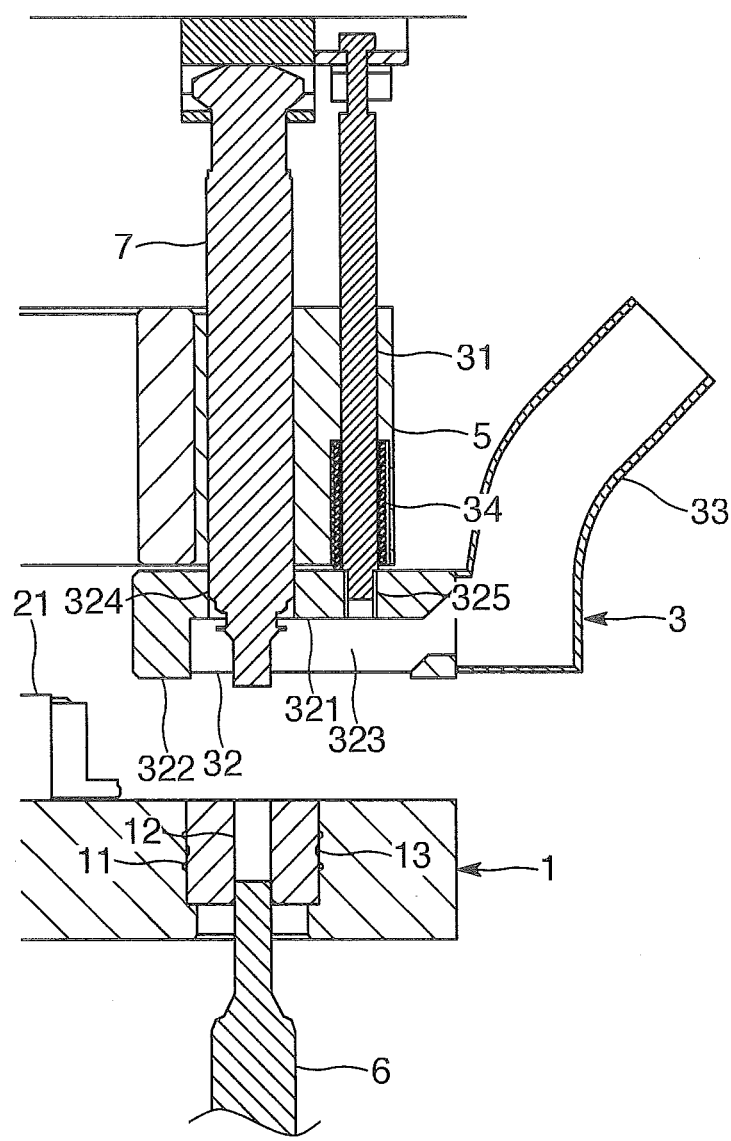
FIG. 3 is an enlarged side sectional view of the principal part in the compression molding machine.
Figure 4:
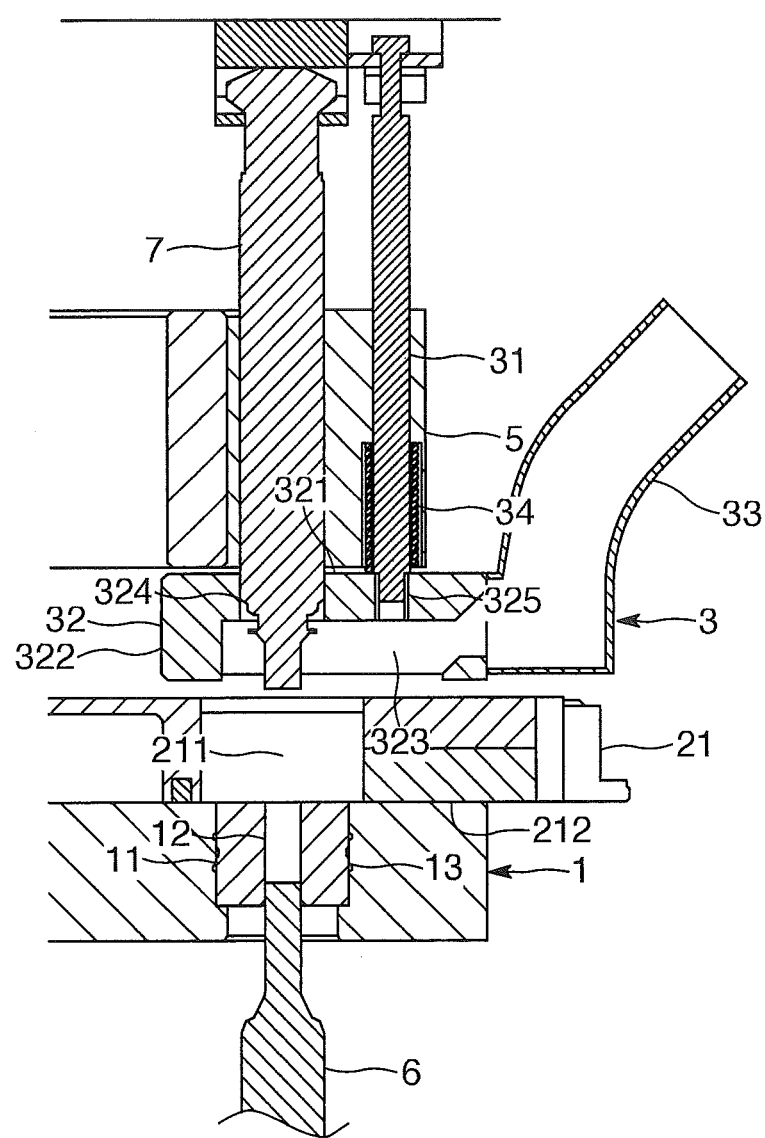
FIG. 4 is an enlarged side sectional view of the principal part in the compression molding machine.
Figure 5:
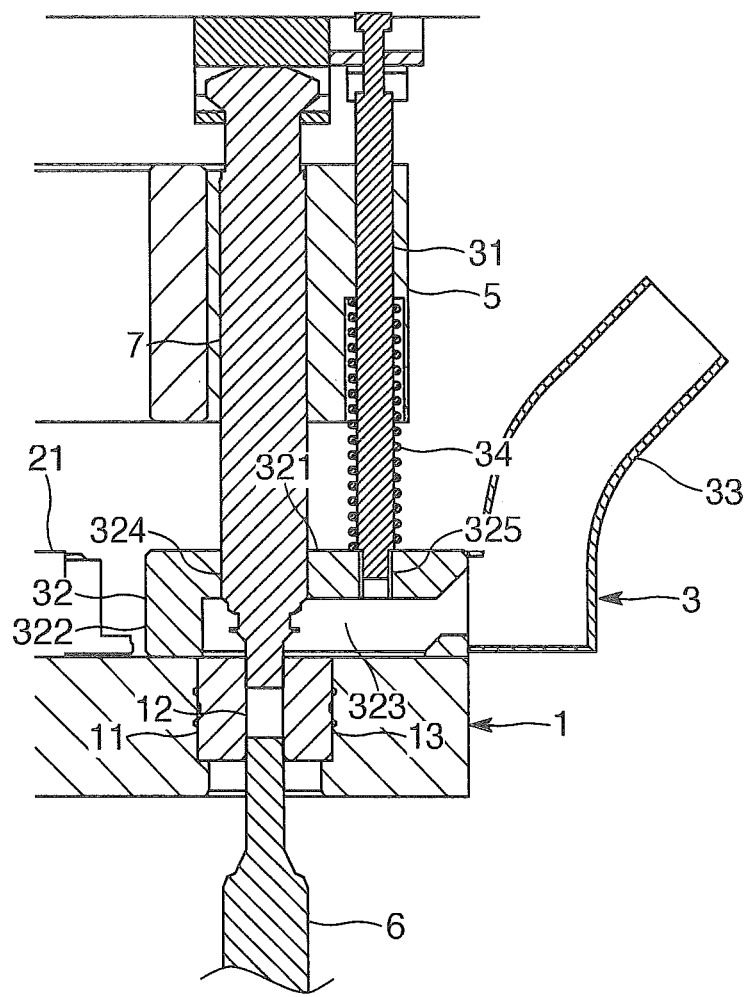
FIG. 5 is an enlarged side sectional view of the principal part in the compression molding machine.

The dust collecting case 32 reciprocates upward and downward between a dust collecting position indicated in FIG. 5 and a retreating position indicated in FIGS. 2 to 4. At the dust collecting position, the upper wall 321 and the side walls 322 of the dust collecting case 32 surround the region around the die bore 12 on the upper surface of the die table 1 so as to isolate the region from the other region. When the lower end of the upper punch 7 is inserted to the die bore 12 to compress the powdery material in the die bore 12, the driver 31 is displaced upward along with the drive source and the upper punch 7 in accordance with the amount of vertical displacement of the upper punch 7 relative to the die table 1 and the die bore 12. In this state, the compression coil spring 34 located between the lower surface of the upper punch retaining portion 5 and the upper surface of the dust collecting case 32 expands appropriately to press the dust collecting case 32 against the upper surface of the die table 1 without applying unreasonable force to the dust collecting case 32.

In contrast, at the retreating position, the dust collecting case 32 floats above the region around the die bore 12 on the upper surface of the die table 1 to open the region. The compression coil spring 34 is compressed because of the reduced distance between the lower surface of the upper punch retaining portion 5 and the upper surface of the dust collecting case 32.

The suction duct 33 is provided continuously from the proximal end of the dust collecting case 32 and extends in a direction different from the reciprocating directions of the feeders 2A, 2B, and 2C when viewed from the die bore 12. The interior of the suction duct 33 communicates with the internal space 323 of the dust collecting case 32. The suction duct 33 is connected to an ejector (a spray pump; not shown) configured to generate suction force. The ejector decompresses the suction duct 33 and the internal space 323 of the dust collecting case 32 with its suction force, so as to suck and remove a powdery material on the die table 1 facing the internal space 323 of the dust collecting case 32. Generation timing and degree of the suction force of the ejector can be controlled by operating a solenoid valve (not shown) that is provided on a flow path between the dust collecting case 32 and the ejector.

Described below is a specific procedure in a method of producing a double layer tablet in the single stroke compression molding machine according to the embodiment.

The feeders 2A, 2B, and 2C are located respectively at the supplying positions at the initial stage in the flow of producing a molded product. Neither the upper punch 7 nor the driver 31 descends, and the lower end of the upper punch 7 is not inserted to the die bore 12. The dust collecting case 32 is located at the retreating position.

A powdery material is initially supplied from the hopper 22 to the filling portion 211 of the feeder 2A located at the supplying position. A first filling step is then executed, in which the feeder 2A moves from the supplying position to the filling position and the powdery material in the filling portion 211 of the feeder 2A is filled into the die bore 12. The feeder 2A does not interfere with any one of the other feeders 2B and 2C, the upper punch 7, and the dust collecting case 32.

The feeder 2A moves from the filling position to the supplying position after the first filling step, while the leveling plate 212 of the feeder 2A levels the powdery material overflown from the upper edge of the die bore 12.

A first compressing step is then executed, in which the upper punch 7 descends, the lower end thereof is inserted to the die bore 12, and the powdery material in the die bore 12 is compressed (preliminarily compressed) between the lower end of the upper punch 7 and the upper end of the lower punch 6. A first layer (lower layer) of the double layer tablet is molded in the first compressing step.

The driver 31, the dust collecting case 32 engaged with the driver 31, and the suction duct 33 connected with the dust collecting case 32 descend along with the descending upper punch 7, and the dust collecting case 32 is located at the dust collecting position. The upper punch 7, the driver 31, and the dust collecting case 32 do not interfere with any one of the feeders 2A, 2B, and 2C in this state. The lower end surfaces of the side walls 322 of the dust collecting case 32 located at the dust collecting position are in close contact with the upper surface of the die table 1. Subsequently executed is a dust collecting step of generating suction force with the ejector to decompress the internal space 323 of the dust collecting case 32 and suck the powdery material remaining in the region around the die bore 12 on the upper surface of the die table 1. Dust collection in this dust collecting step is executed simultaneously with powdery material compression in the first compressing step. This shortens the steps of producing the compression molded product.

After the first compressing step and the dust collecting step, the upper punch 7, the driver 31, the dust collecting case 32, and the suction duct 33 ascend, so that the lower end of the upper punch 7 is extracted from the die bore 12 and the suction duct 33 moves to the retreating position.

A powdery material is subsequently supplied from the hopper 22 to the filling portion 211 of the feeder 2B located at the supplying position. A second filling step is then executed, in which the feeder 2B moves from the supplying position to the filling position and the powdery material in the filling portion 211 of the feeder 2B is filled into the die bore 12. The feeder 2B does not interfere with any one of the other feeders 2A and 2C, the upper punch 7, and the dust collecting case 32.

The leveling plate 212 of the feeder 2B levels the powdery material overflown from the upper edge of the die bore 12, while the feeder 2B moves from the filling position to the supplying position after the second filling step.

A second compressing step is then executed, in which the upper punch 7 descends, the lower end thereof is inserted to the die bore 12, and the powdery material in the die bore 12 is compressed (mainly compressed, or preliminarily and mainly compressed) between the lower end of the upper punch 7 and the upper end of the lower punch 6. A second layer (upper layer) of the double layer tablet is molded in the second compressing step and the double layer tablet is thus completed.

Figure 7:
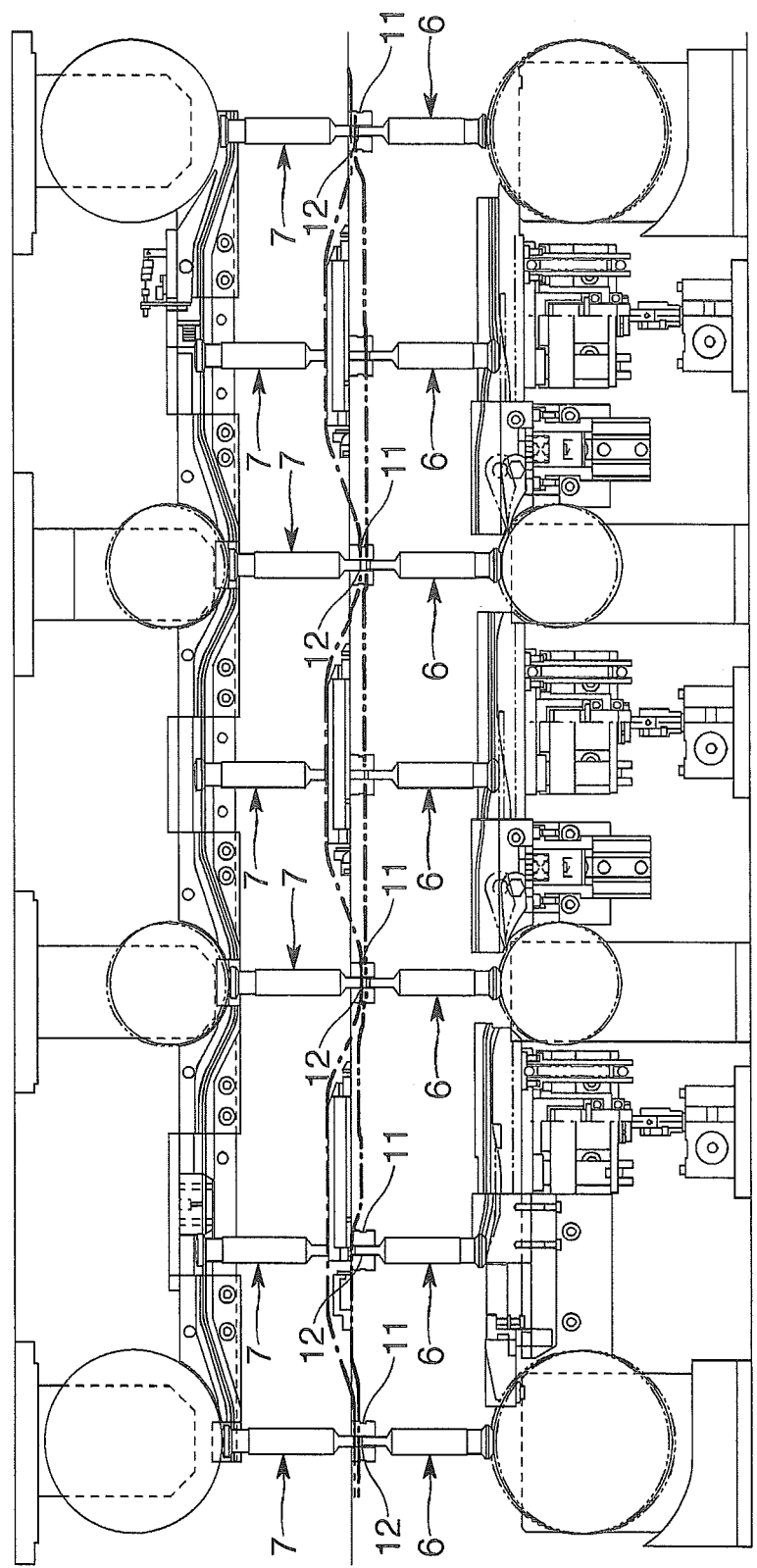
FIG. 7 is a center development view of a rotary compression molding machine including dies and punches same as those of the compression molding machine according to the invention.

FIG. 7 is a center development view of an ordinary rotary compression molding machine configured to produce a triple layer tablet. The rotary compression molding machine has a basic configuration similar to that of a known machine.

Figure 8:
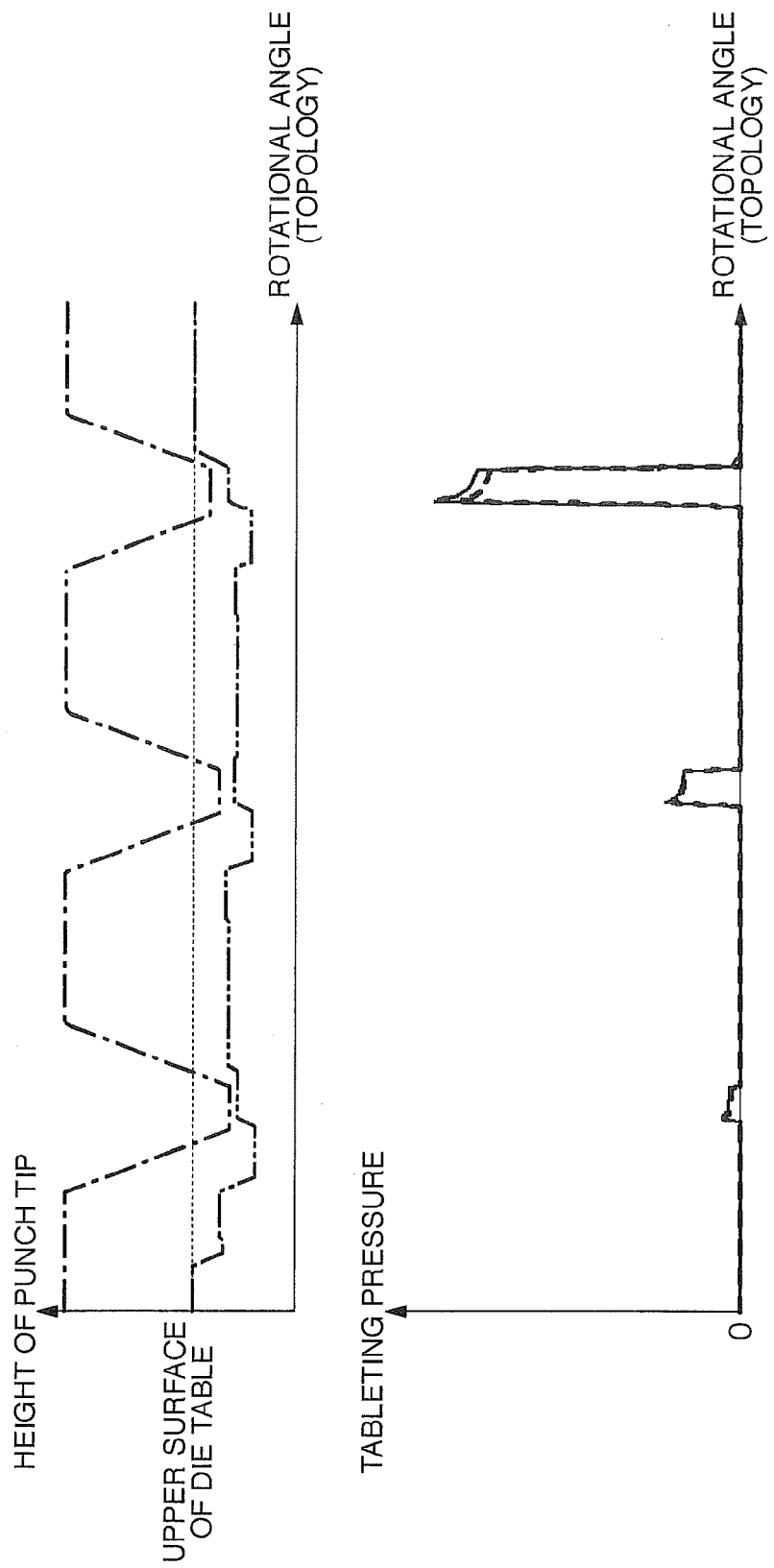
FIG. 8 includes graphs indicating loci of the displaced upper and lower punches in the rotary compression molding machine as well as changes in tableting pressure by these punches.

FIG. 8 indicates loci of displacement in height of the upper and lower punches 7 and 6 in the single stroke compression molding machine as well as changes in tableting pressure by the upper and lower punches 7 and 6. In FIG. 8, height of the tip of the upper punch 7 is indicated by the bold dashed line and pressure applied to the upper punch 7 is indicated by the broken line. Furthermore, height of the tip of the lower punch 6 is indicated by the bold two-dot chain line and pressure applied to the lower punch 6 is indicated by the solid line.

The drive source such as a servo motor configured to drive each of the upper and lower punches 7 and 6 in the single stroke compression molding machine according to the embodiment operates to simulatively achieve the loci of displacement of the punches 7 and 6 as well as the changes in tableting pressure by the punches 7 and 6 indicated in FIG. 7. In other words, the single stroke compression molding machine achieves a tableting condition equivalent to that for the rotary compression molding machine.

The driver 31, the dust collecting case 32, and the suction duct 33 descend along with the descending upper punch 7, and the dust collecting case 32 is located at the dust collecting position. The upper punch 7, the driver 31, and the dust collecting case 32 do not interfere with any one of the feeders 2A, 2B, and 2C in this state. The lower end surfaces of the side walls 322 of the dust collecting case 32 located at the dust collecting position are in close contact with the upper surface of the die table 1. Subsequently executed is the dust collecting step of generating suction force with the ejector to decompress the internal space 323 of the dust collecting case 32 and suck the powdery material remaining in the region around the die bore 12 on the upper surface of the die table 1 as well as other dust and dirt. Dust collection in this dust collecting step is executed simultaneously with powdery material compression in the second compressing step.

After the second compressing step and the dust collecting step, the upper punch 7, the driver 31, the dust collecting case 32, and the suction duct 33 ascend, so that the lower end of the upper punch 7 is extracted from the die bore 12 and the suction duct 33 is returned to the retreating position.

An ejecting step is lastly executed, in which the lower punch 6 is ascended and the compression molded product is ejected out of the die bore 12 with the upper end of the lower punch 6.

In the case of producing a triple layer tablet in the single stroke compression molding machine according to the embodiment, a third filling step, a third compressing step, and a dust collecting step to be described below are added after the second compressing step (preliminarily compression) and the dust collecting step and before the ejecting step of ejecting the molded product in the method of producing a double layer tablet.

A powdery material is supplied from the hopper 22 to the filling portion 211 of the feeder 2C located at the supplying position in the third filling step. The feeder 2C then moves from the supplying position to the filling position, and the powdery material in the filling portion 211 of the feeder 2C is filled into the die bore 12. The feeder 2C does not interfere with any one of the other feeders 2A and 2B, the upper punch 7, and the dust collecting case 32.

The leveling plate 212 of the feeder 2C levels the powdery material overflown from the upper edge of the die bore 12, while the feeder 2C moves from the filling position to the supplying position after the third filling step.

In the third compressing step, the upper punch 7 descends and the lower end thereof is inserted to the die bore 12. The powdery material in the die bore 12 is thus compressed (mainly compressed, or preliminarily and mainly compressed) between the lower end of the upper punch 7 and the upper end of the lower punch 6. A third layer (uppermost layer) of the triple layer tablet is molded in the third compressing step and the triple layer tablet is thus completed.

The loci of the tips of the lower and upper punches 6 and 7 are made as shown in FIG. 8 so as to approximate to the loci of the lower and upper punches in the rotary compression molding machine applied for production of a triple layer tablet shown in FIG. 7. This configuration achieves approximation to a compression molding condition for the rotary compression molding machine.

In the dust collecting step, the driver 31, the dust collecting case 32, and the suction duct 33 descend along with the descending upper punch 7, and the dust collecting case 32 is located at the dust collecting position. The upper punch 7, the driver 31, and the dust collecting case 32 do not interfere with any one of the feeders 2A, 2B, and 2C in this state. The lower end surfaces of the side walls 322 of the dust collecting case 32 located at the dust collecting position are in close contact with the upper surface of the die table 1. Subsequently, the ejector generates suction force to decompress the internal space 323 of the dust collecting case 32 and suck the powdery material remaining in the region around the die bore 12 on the upper surface of the die table 1. Dust collection in this dust collecting step is executed simultaneously with powdery material compression in the third compressing step.

Executed after the second compressing step and the dust collecting step is the ejecting step of ejecting the compression molded product out of the die bore 12.

According to the embodiment, the single stroke compression molding machine includes: the die table 1 having the die bore 12 penetrating vertically; the slidable lower punch 6 located below the die bore 12 and having the upper end to be inserted to the die bore 12; the slidable upper punch 7 located above the die bore 12 to face the lower punch 6 and having the lower end to be inserted to the die bore 12; the feeders 2A, 2B, and 2C each configured to fill the die bore 12 with a powdery material to be compression molded by the lower and upper punches 6 and 7; and the dust collector 3 configured to collect dust on the upper surface of the die table 1 in a state where the lower end of the upper punch 7 is located in the die bore 12.

The method of producing a compression molded product according to the embodiment relates to a method of producing a molded product by compression molding a powdery material filled in the die bore 12 provided in the die table 1 with the lower punch 6 having the upper end inserted to the die bore 12 and the upper punch 7 having the lower end inserted to the die bore 12, and the method includes collecting dust on the upper surface of the die table 1 in a state where the lower end of the upper punch 7 is located in the die bore 12.

According to the embodiment, dust on the upper surface of the die table 1 is collected while the upper and lower punches 7 and 6 compression mold the powdery material in the die bore 12. The embodiment thus achieves inhibition of contamination by the powdery materials for the respective layers of the double layer tablet or the triple layer tablet as well as reduction in time required for production of a single molded product.

The lower and upper punches 6 and 7 are also applicable to a rotary compression molding machine. A product developed with the single stroke compression molding machine according to the embodiment can be thus mass produced easily by the rotary compression molding machine on a larger scale. Furthermore, whether or not imperfect tableting occurs can be checked beforehand at the research and development stage.

According to the embodiment, the compression molding machine includes: the die table 1 having the die bore 12 penetrating vertically; the slidable lower punch 6 located below the die bore 12 and having the upper end to be inserted to the die bore 12; the slidable upper punch 7 located above the die bore 12 to face the lower punch 6 and having the lower end to be inserted to the die bore 12; the feeders 2A, 2B, and 2C each configured to fill the die bore 12 with a powdery material to be compression molded by the lower and upper punches 6 and 7; and the dust collector 3 configured to collect dust on the upper surface of the die table 1; wherein the dust collector 3 includes the driver 31 configured to move upward or downward along with the upper punch 7, the dust collecting case 32 engaged with the driver 31 and configured to move upward or downward, in accordance with upward or downward movement of the driver 31, between the dust collecting position where the dust collecting case 32 covers the region around the die bore 12 on the upper surface of the die table 1 and the retreating position where the dust collecting case 32 is distant above from the upper surface of the die table 1, and the suction duct 33 connected to the dust collecting case 32 and configured to decompress the internal space 323 of the dust collecting case 32. The dust collecting case 32 can be moved to the retreating position when a powdery material is filled into the die bore 12, so as not to interfere with any one of the feeders 2A, 2B, and 2C. Locating the dust collector 3 vertically above the die bore 12 achieves reduction in space as well as upward suction of the powdery material remaining on the upper surface of the die table 1 in the dust collecting step. The region around the die bore 12 can be cleaned sufficiently in the state where the upper punch 7 is located in the die bore 12.

The single stroke compression molding machine, which includes at least two feeders, can easily produce a compression molded product having a plurality of layers, by supplying the feeder 2A with a powdery material for the first layer and supplying the feeder 2B with a powdery material for the second layer (as well as supplying the feeder 2C with a powdery material for the third layer for production of a triple layer tablet).

Figure 6:
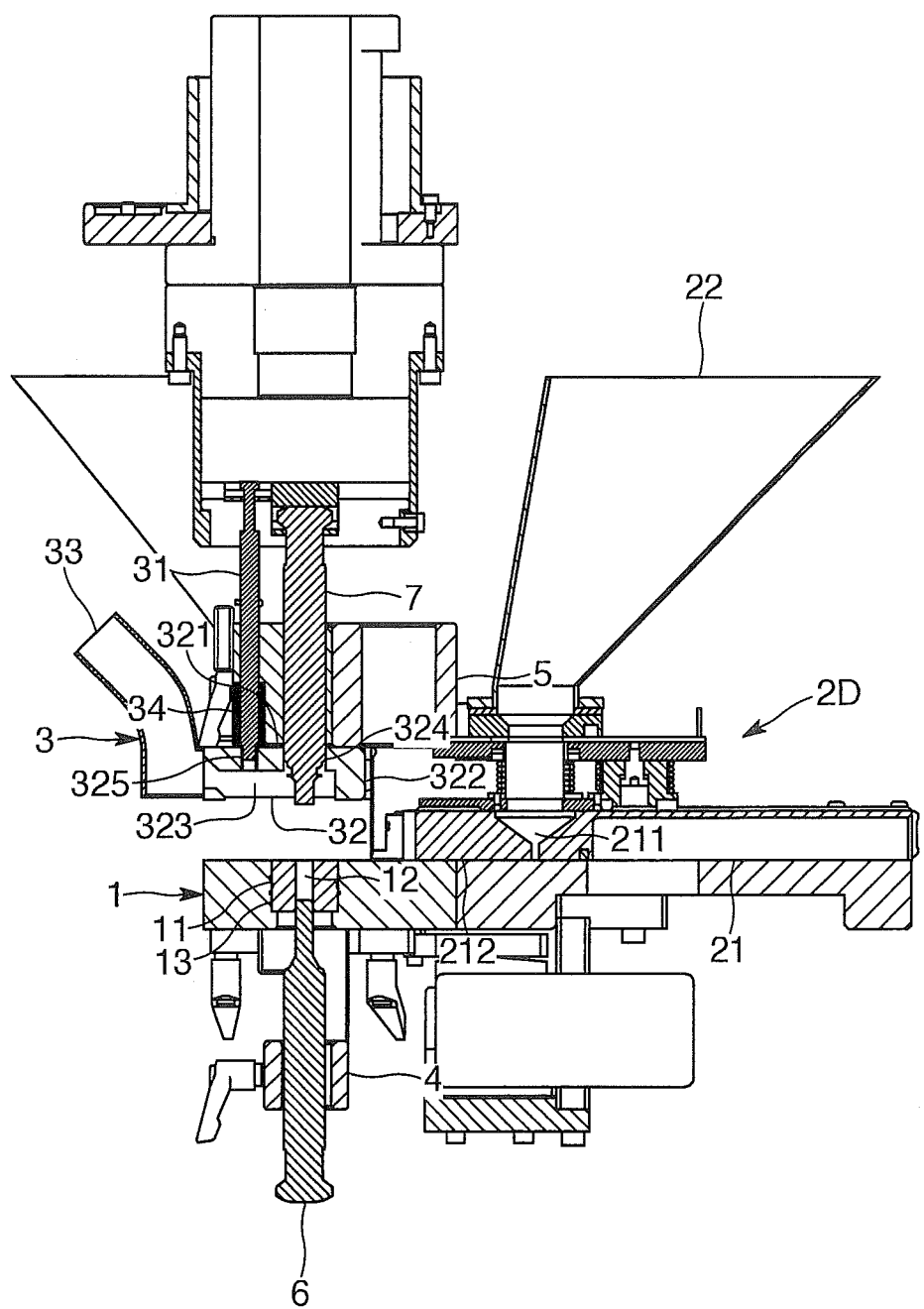
FIG. 6 is a side sectional view of a principal part in a single stroke compression molding machine according to an modification example of the invention.

When the single stroke compression molding machine according to the embodiment produces a dry-coated tablet, one of the feeders 2A, 2B, and 2C is replaced with a supplier 2D configured to supply the die bore 12 with a core (an internal core or a core tablet) to be buried in the dry-coated tablet, as shown in FIG. 6.

Described below is a specific procedure in a method of producing a dry-coated tablet in the single stroke compression molding machine described above. A powdery material is initially supplied from the hopper 22 to the filling portion 211 of the feeder 2A located at the supplying position. The first filling step is then executed, in which the feeder 2A moves from the supplying position to the filling position and the powdery material in the filling portion 211 of the feeder 2A is filled into the die bore 12.

The leveling plate 212 of the feeder 2A levels to remove the powdery material overflown from the upper edge of the die bore 12, while the feeder 2A moves from the filling position to the supplying position after the first filling step.

The first compressing step is then executed, in which the upper punch 7 descends, the lower end thereof is inserted to the die bore 12, and the powdery material in the die bore 12 is compressed (preliminarily compressed) between the lower end of the upper punch 7 and the upper end of the lower punch 6. This compressing step is not essentially included. The upper punch 7 is inserted to the die bore 12 but the powdery material may be compressed slightly or may never be compressed.

The driver 31, the dust collecting case 32 engaged with the driver 31, and the suction duct 33 connected with the dust collecting case 32 descend along with the descending upper punch 7, and the dust collecting case 32 is located at the dust collecting position. The lower end surfaces of the side walls 322 of the dust collecting case 32 located at the dust collecting position are in close contact with the upper surface of the die table 1. Subsequently executed is the dust collecting step of generating suction force with the ejector to decompress the internal space 323 of the dust collecting case 32 and suck the powdery material remaining in the region around the die bore 12 on the upper surface of the die table 1.

After the first compressing step and the dust collecting step, the upper punch 7, the driver 31, the dust collecting case 32, and the suction duct 33 ascend, so that the lower end of the upper punch 7 is extracted from the die bore 12 and the suction duct 33 moves to the retreating position.

A core is subsequently supplied from a part feeder 24 to the supplier 2D located at the supplying position. The core supplying step is then executed, in which the supplier 2D moves from the supplying position to a core supplying position (the filling position) and the core in the supplier 2D is filled into the die bore 12.

A powdery material is also supplied from the hopper 22 to the filling portion 211 of the feeder 2B located at the supplying position. The second filling step is then executed, in which the feeder 2B moves from the supplying position to the filling position and the powdery material in the filling portion 211 of the feeder 2B is filled into the die bore 12. The core already supplied into the die bore 12 is coated with the powdery material in the second filling step.

The feeder 2B moves from the filling position to the supplying position after the second filling step.

The second compressing step is then executed, in which the upper punch 7 descends, the lower end thereof is inserted to the die bore 12, and the powdery material in the die bore 12 is compressed (mainly compressed, or preliminarily and mainly compressed) between the lower end of the upper punch 7 and the upper end of the lower punch 6. The dry-coated tablet is completed in the second compressing step.

The driver 31, the dust collecting case 32, and the suction duct 33 descend along with the descending upper punch 7, and the dust collecting case 32 is located at the dust collecting position. The lower end surfaces of the side walls 322 of the dust collecting case 32 located at the dust collecting position are in close contact with the upper surface of the die table 1. Subsequently executed is the dust collecting step of generating suction force with the ejector to decompress the internal space 323 of the dust collecting case 32 and suck the powdery material remaining in the region around the die bore 12 on the upper surface of the die table 1. Dust collection in this dust collecting step is executed simultaneously with powdery material compression in the second compressing step.

After the second compressing step and the dust collecting step, the upper punch 7, the driver 31, the dust collecting case 32, and the suction duct 33 ascend, so that the lower end of the upper punch 7 is extracted from the die bore 12 and the suction duct 33 moves to the retreating position.

The ejecting step is lastly executed, in which the lower punch 6 is ascended and the compression molded product is ejected out of the die bore 12 with the upper end of the lower punch 6.

The invention is not limited to the embodiments described above. The dust collecting case 32 according to the above embodiment is moved upward and downward, however, the dust collecting case 32 can be slid along the upper surface of the die table 1, similarly to the feeder 2A, 2B, or 2C or the supplier 2D, for example.

Specific configurations of the other portions can be modified in various manners within the scope not departing from the purposes of the invention.

What is claimed is:

1. A single stroke compression molding machine, comprising:
    a die table comprising a die bore penetrating vertically;
    a slidable lower punch located below the die bore and comprising an upper end to be inserted to the die bore;
    a slidable upper punch located above the die bore to face the lower punch and comprising a lower end to be inserted to the die bore;
    a feeder configured to fill the die bore with a powdery material to be compression molded by the lower and upper punches;
    a dust collector configured to collect dust on an upper surface of the die table in a state where the lower end of the upper punch is located in the die bore; and
    at least two feeders,
    wherein, after one of the feeders fills the die bore with the powdery material, the dust collector collects the dust on the upper surface of the die table while the lower end of the upper punch is inserted in the die bore to compress the powdery material fed by said one of the feeders.

2. The single stroke compression molding machine according to claim 1, wherein the lower and upper punches are applicable to a rotary compression molding machine.

3. The single stroke compression molding machine according to claim 1, the machine being configured to produce a molded product comprising a core inside the powdery material, and the machine comprising:
    a supplier configured to supply the die bore with the core.

4. The single stroke compression molding machine according to claim 2, the machine being configured to produce a molded product comprising a core inside the powdery material, and the machine comprising:
    a supplier configured to supply the die bore with the core.

5. A single stroke compression molding machine, comprising:
    a die table comprising a die bore penetrating vertically;
    a slidable lower punch located below the die bore and comprising an upper end to be inserted to the die bore;
    a slidable upper punch located above the die bore to face the lower punch and comprising a lower end to be inserted to the die bore;
    a feeder configured to fill the die bore with a powdery material to be compression molded by the lower and upper punches; and
    a dust collector configured to collect dust on an upper surface of the die table,
    wherein the dust collector includes:
        a driver configured to move upward or downward along with the upper punch;
        a dust collecting case engaged with the driver and configured to move upward or downward, in accordance with upward or downward movement of the driver, between a dust collecting position where the dust collecting case covers a region around the die bore on the upper surface of the die table and a retreating position where the dust collecting case is distant above from the upper surface of the die table; and a suction duct connected to the dust collecting case and configured to decompress an internal space of the dust collecting case.

6. The single stroke compression molding machine according to claim 1, wherein the dust collector comprises a driver configured to move upward or downward along with the upper punch.

7. The single stroke compression molding machine according to claim 6, wherein the dust collector further comprises a dust collecting case engaged with the driver and configured to move upward or downward, in accordance with upward or downward movement of the driver.

8. The single stroke compression molding machine according to claim 6, wherein the dust collector further comprises a dust collecting case engaged with the driver and configured to move upward or downward, in accordance with upward or downward movement of the driver, between a dust collecting position where the dust collecting case covers a region around the die bore on the upper surface of the die table and a retreating position where the dust collecting case is distant above from the upper surface of the die table.

9. The single stroke compression molding machine according to claim 1, wherein the dust collector further comprises a dust collecting case configured to move upward or downward between a dust collecting position where the dust collecting case covers a region around the die bore on the upper surface of the die table and a retreating position where the dust collecting case is distant above from the upper surface of the die table.

10. The single stroke compression molding machine according to claim 5, the machine being configured to produce a molded product comprising a core inside the powdery material, and the machine comprising:

a supplier configured to supply the die bore with the core.

11. The single stroke compression molding machine according to claim 5, wherein the feeder comprises at least two feeders.

12. The single stroke compression molding machine according to claim 11, the machine being configured to produce a molded product comprising a core inside the powdery material, and the machine comprising:

a supplier configured to supply the die bore with the core.

13. A method of producing a molded product in a single stroke compression molding machine, comprising at least two feeders, by compression molding a powdery material filled in a die bore provided in a die table with a lower punch comprising an upper end inserted to the die bore and an upper punch comprising a lower end inserted to the die bore, the method comprising:

after one of the feeders fills the die bore with the powdery material, collecting dust on an upper surface of the die table in a state where the lower end of the upper punch is located in the die bore to compress the powdery material fed by said one of the feeders.

14. The method according to claim 13, wherein the dust collector comprises a driver configured to move upward or downward along with the upper punch.

15. The method according to claim 14, wherein the dust collector further comprises a dust collecting case engaged with the driver and configured to move upward or downward, in accordance with upward or downward movement of the driver.

16. The method according to claim 14, wherein the dust collector further comprises a dust collecting case engaged with the driver and configured to move upward or downward, in accordance with upward or downward movement of the driver, between a dust collecting position where the dust collecting case covers a region around the die bore on the upper surface of the die table and a retreating position where the dust collecting case is distant above from the upper surface of the die table.

* * * * *